(12) United States Patent
Dubach et al.

(10) Patent No.: US 7,966,699 B2
(45) Date of Patent: Jun. 28, 2011

(54) SHUTTER (OR DOOR) FITTING

(75) Inventors: Fredi Dubach, Bäretwil (CH); Harald Brunnmayr, Hörbranz (AT)

(73) Assignee: Julius Blum GmbH, Höchst (AT)

( * ) Notice: Subject to any disclaimer, the term of this patent is extended or adjusted under 35 U.S.C. 154(b) by 0 days.

(21) Appl. No.: 12/081,001

(22) Filed: Apr. 9, 2008

(65) Prior Publication Data

US 2008/0209682 A1 Sep. 4, 2008

Related U.S. Application Data

(63) Continuation of application No. PCT/AT2006/000415, filed on Oct. 10, 2006.

(30) Foreign Application Priority Data

Oct. 12, 2005 (AT) .................. A 1659/2005

(51) Int. Cl.
*E05D 5/10* (2006.01)
(52) U.S. Cl. ............ 16/386; 16/252; 16/254; 16/260; 16/366; 16/382; 16/258; 16/259
(58) Field of Classification Search .......... 16/240, 16/242, 252, 254, 260, 272, 366, 382, 388, 16/386, 265, 281, 266, 258, 259, 271, 279, 16/287, 294, 297, 302, 319, 324, 321, 327, 16/331, 332, 286, 326, 349; 292/95, 96, 292/101, 102, 108, 194, 195, 202, 203, 210, 292/304
See application file for complete search history.

(56) References Cited

U.S. PATENT DOCUMENTS

| | | | | | |
|---|---|---|---|---|---|
| 4,430,771 | A | * | 2/1984 | Salice | 16/235 |
| 4,800,621 | A | * | 1/1989 | Rock et al. | 16/235 |
| 5,056,189 | A | * | 10/1991 | Brustle et al. | 16/235 |
| 5,056,190 | A | * | 10/1991 | Rock et al. | 16/240 |
| 5,058,239 | A | * | 10/1991 | Lee | 16/324 |
| 5,105,506 | A | * | 4/1992 | Lin | 16/258 |

(Continued)

FOREIGN PATENT DOCUMENTS

DE 27 52 186 6/1979
(Continued)

OTHER PUBLICATIONS

International Search Report issued Feb. 12, 2007 in the International (PCT) Application of which the present application is the U.S. National Stage.

(Continued)

*Primary Examiner* — Thomas B Will
*Assistant Examiner* — Emily M Morgan
(74) *Attorney, Agent, or Firm* — Wenderoth, Lind & Ponack, L.L.P.

(57) ABSTRACT

Shutter (or door) fitting for fastening a furniture shutter (or door) in a pivotable manner on a basic cabinet structure, having at least one actuating arm, which is provided for moving the furniture shutter, and having at least one shutter-mounted fitting part, which can be connected to the actuating arm, characterized in that the shutter-mounted fitting part has a rotation-prevention means for temporarily fixing the pivoting position of the at least one actuating arm, preferably in the fully open position thereof, wherein the rotation-prevention means, in a first operating position, arrests the at least one actuating arm in its pivoting position relative to the shutter-mounted fitting part and, in a second operating position, allows the actuating arm to pivot.

13 Claims, 14 Drawing Sheets

U.S. PATENT DOCUMENTS

| | | | |
|---|---|---|---|
| 6,034,867 A * | 3/2000 | Seo ........................... | 361/679.27 |
| 7,080,428 B2 * | 7/2006 | Hyde .............................. | 16/265 |
| 7,178,199 B2 * | 2/2007 | Kashiwaguma ................ | 16/258 |
| 7,178,202 B2 * | 2/2007 | Hirtsiefer et al. ................ | 16/366 |
| 7,490,385 B2 * | 2/2009 | Migli .............................. | 16/246 |
| 2004/0239213 A1 | 12/2004 | Hirtsiefer | |

FOREIGN PATENT DOCUMENTS

| | | |
|---|---|---|
| DE | 29 34 506 | 3/1981 |
| DE | 37 18 730 | 12/1988 |
| DE | 200 17 906 | 4/2001 |
| EP | 1 296 011 | 3/2003 |
| ES | 2 156 656 | 7/2001 |
| FR | 2 089 842 | 1/1972 |

OTHER PUBLICATIONS

Austrian Search Report issued May 10, 2006 in the corresponding Austrian patent application.

* cited by examiner

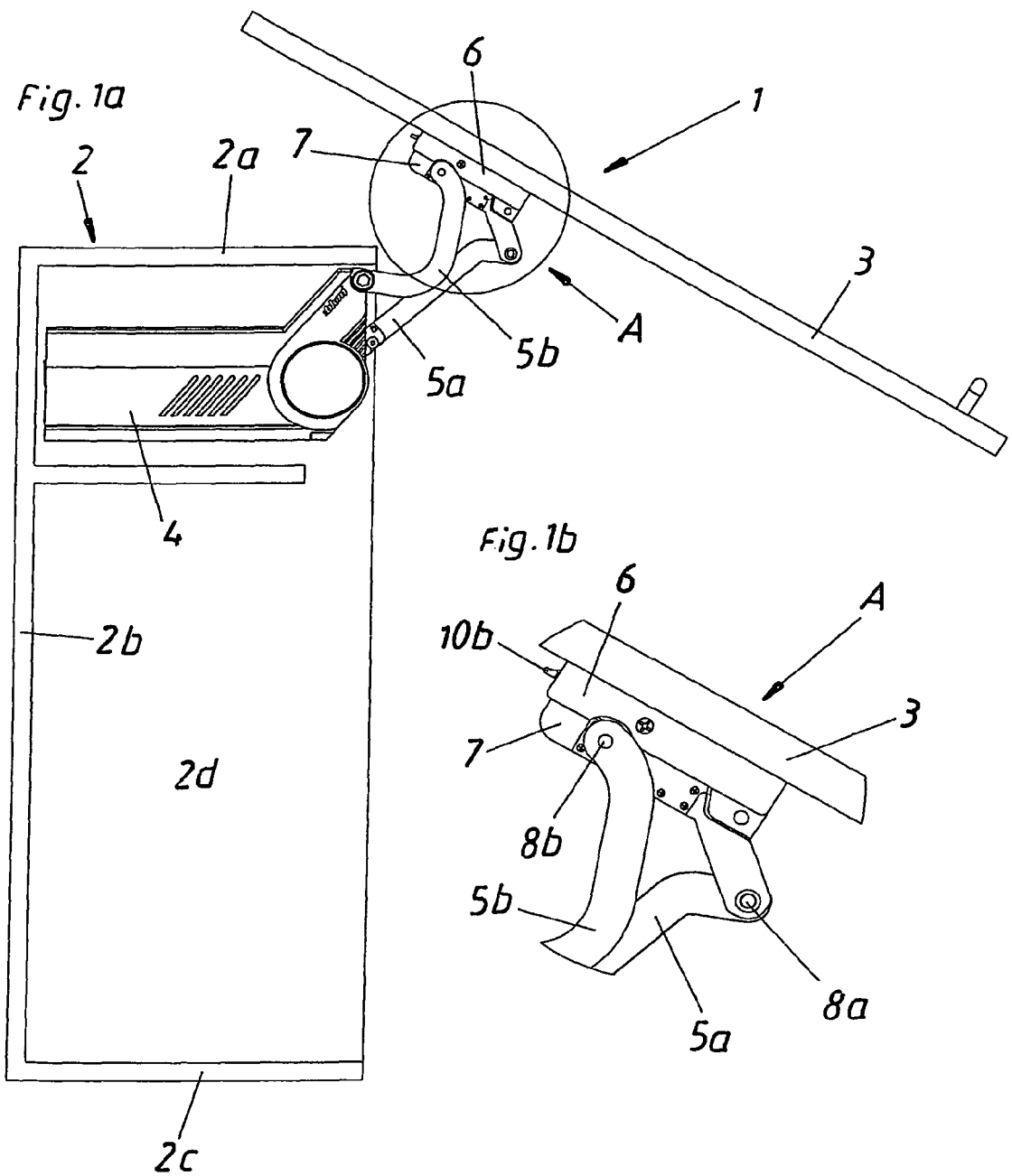

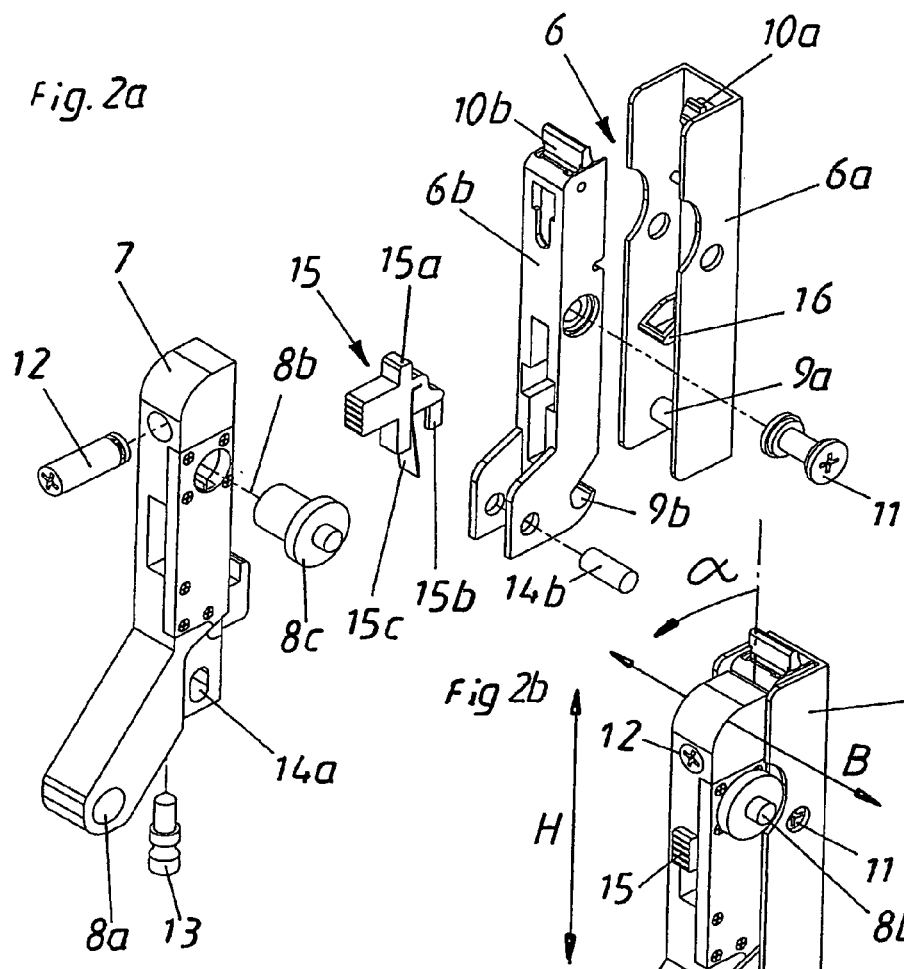
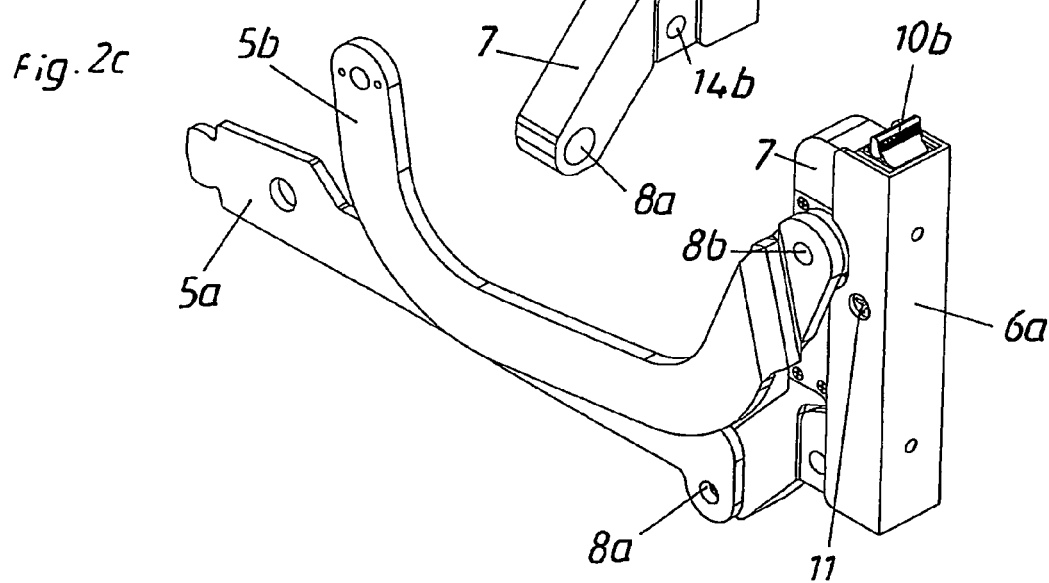

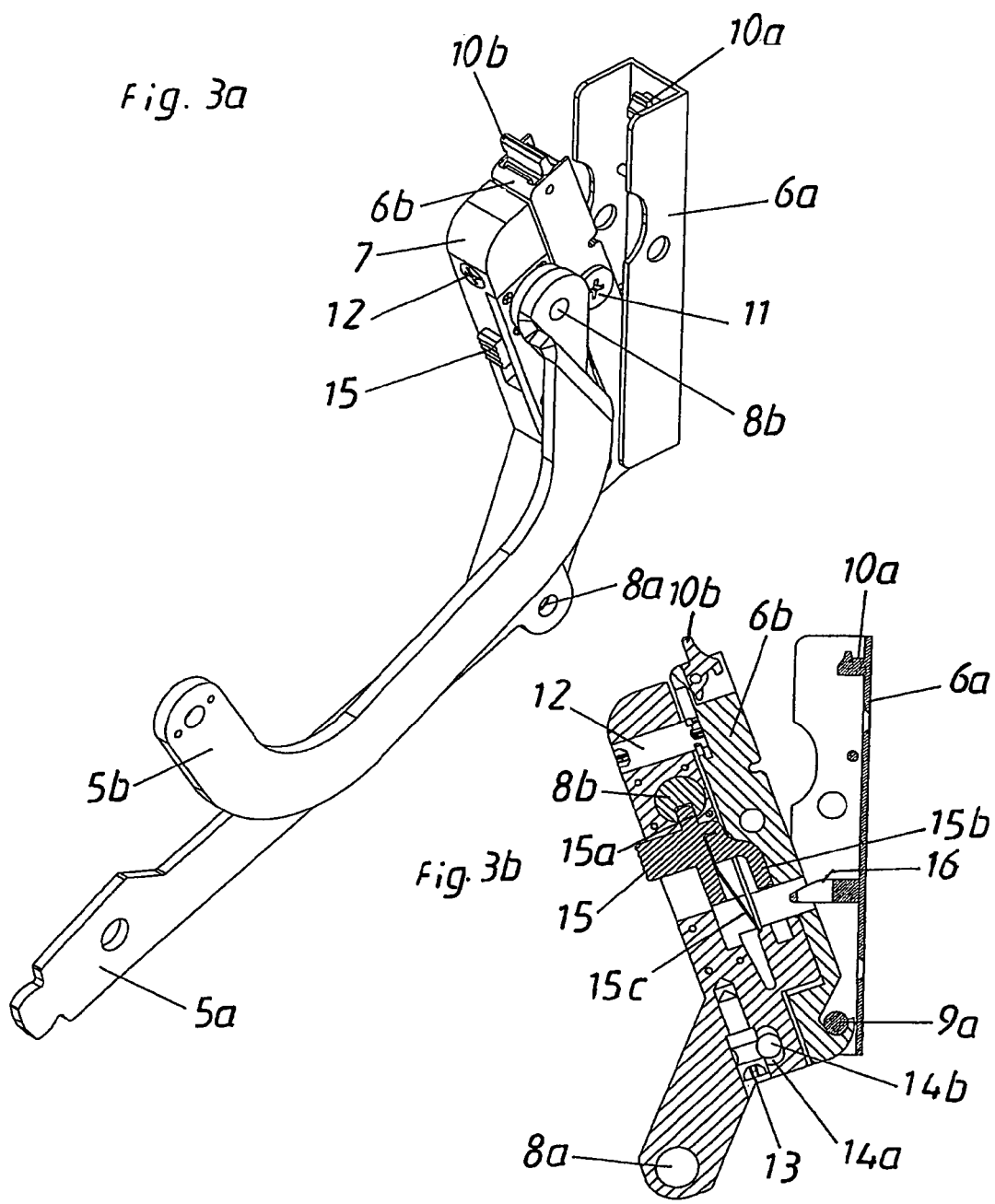

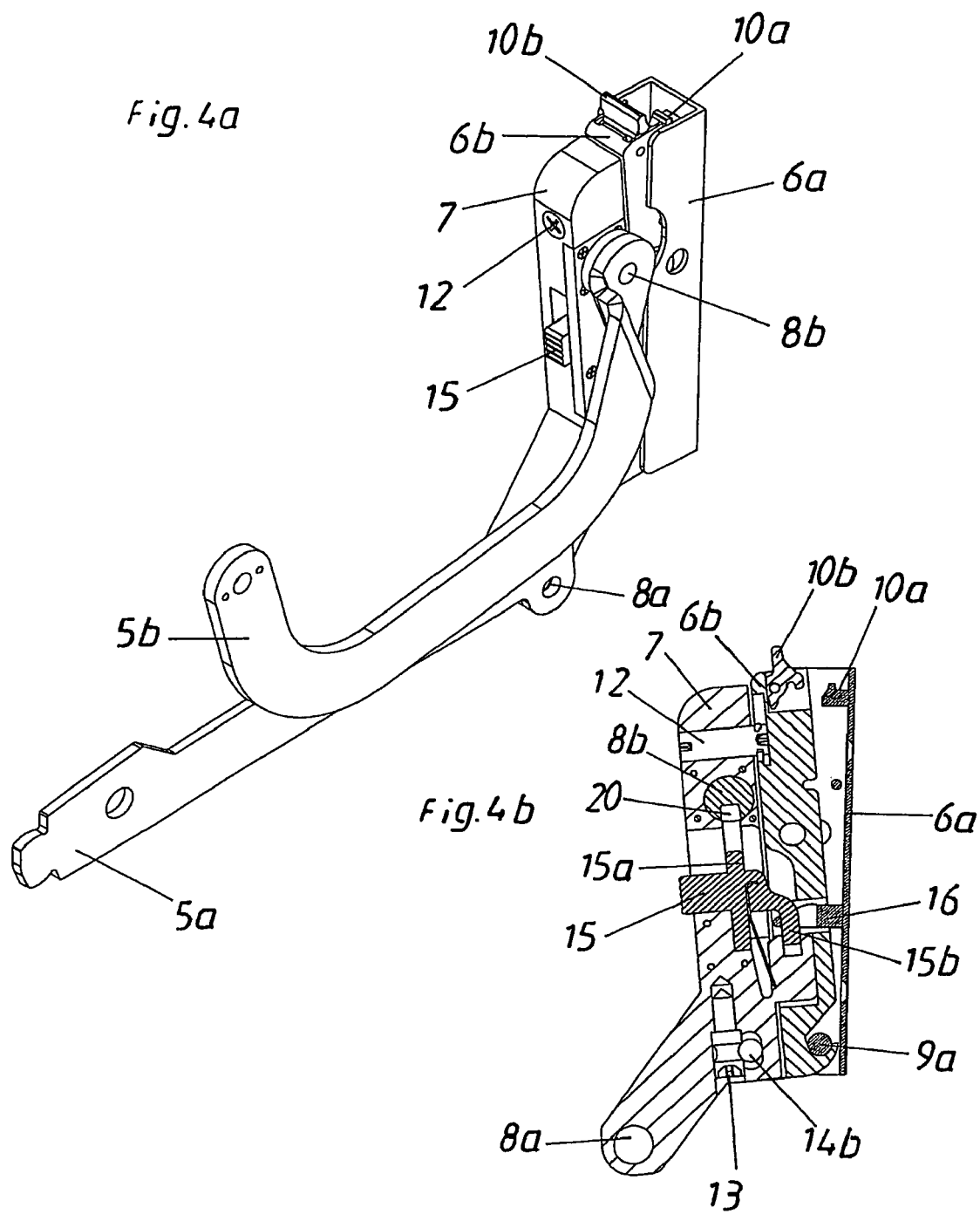

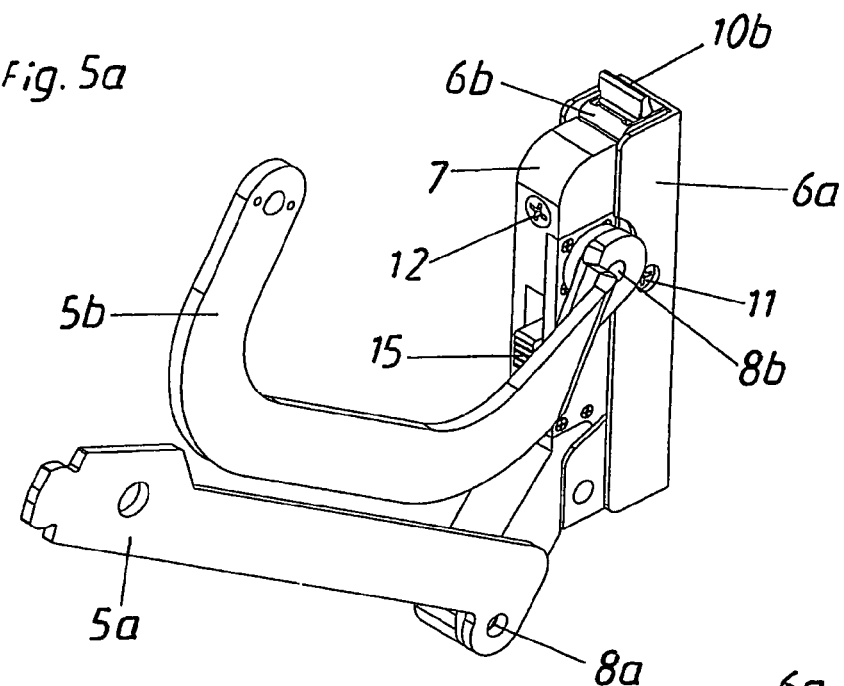
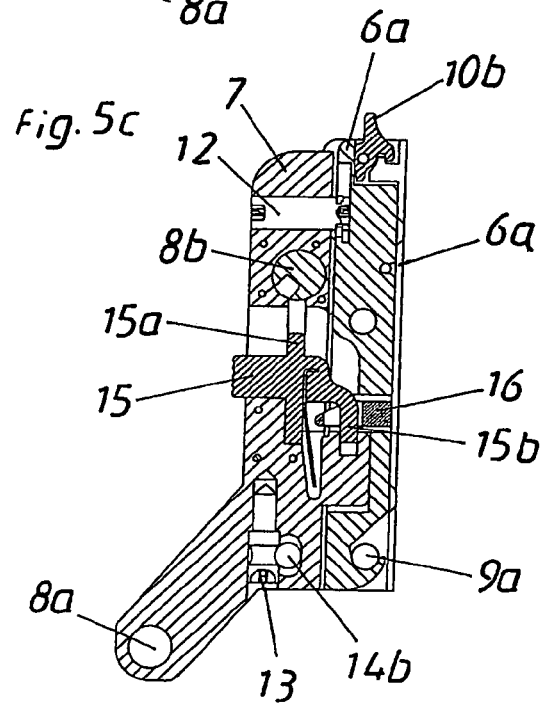
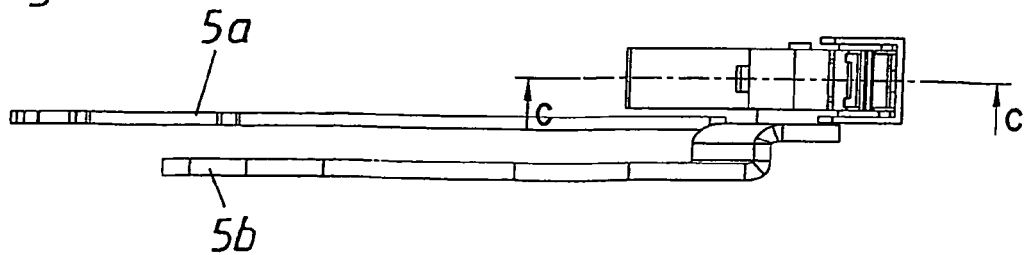

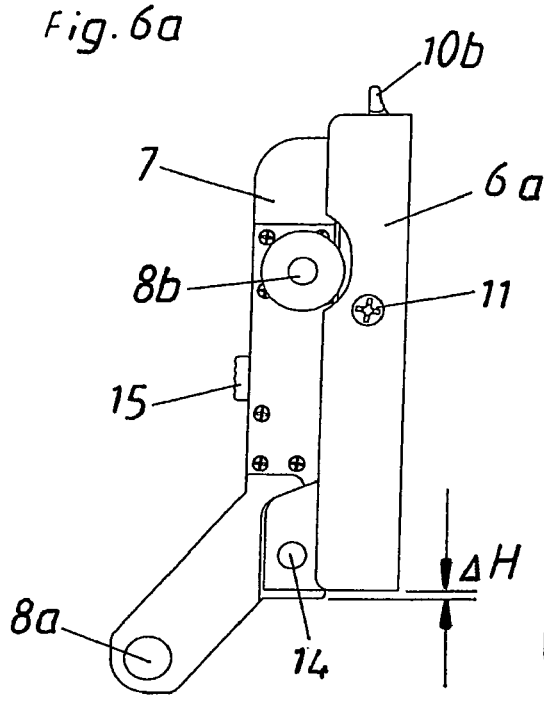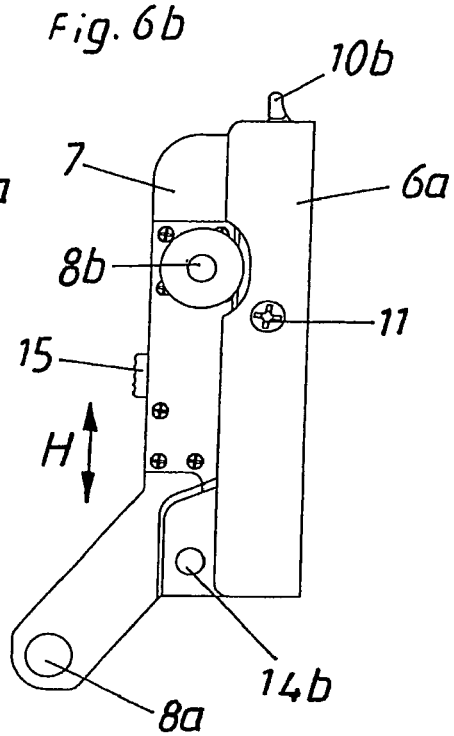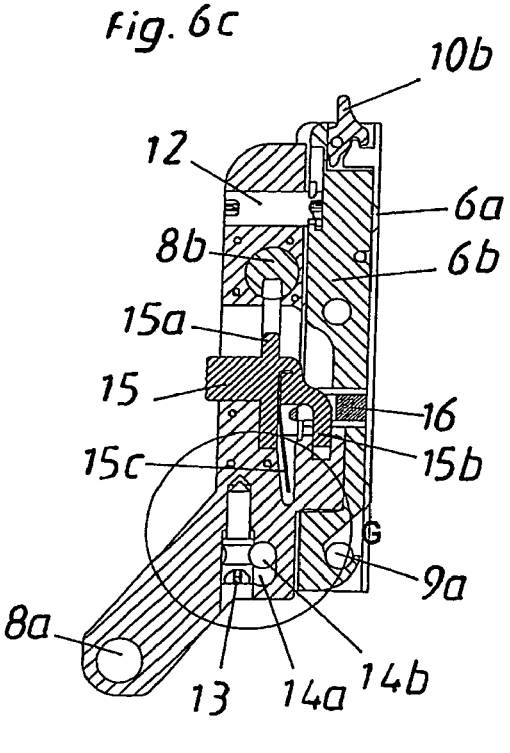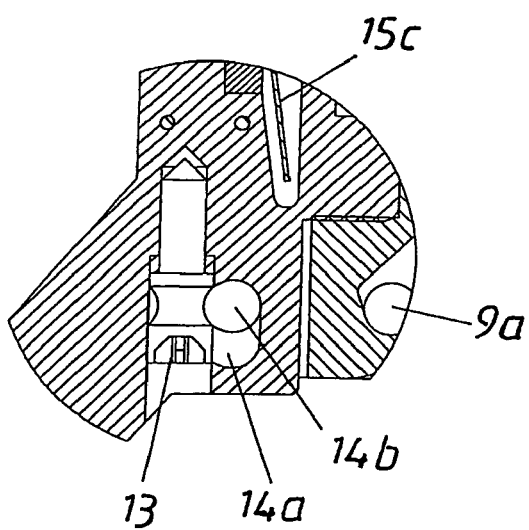

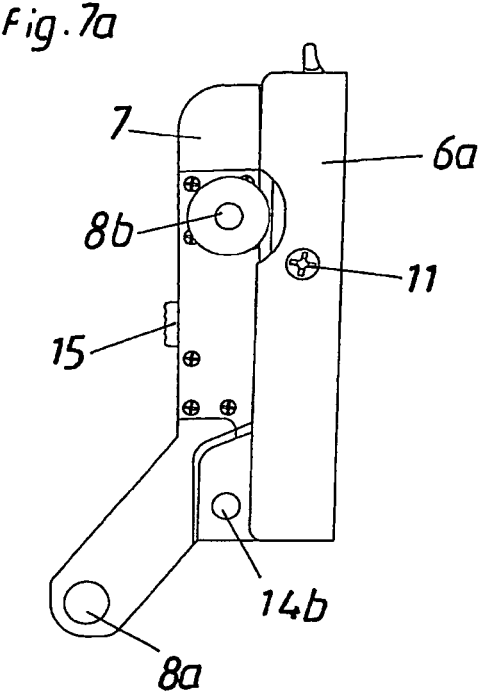
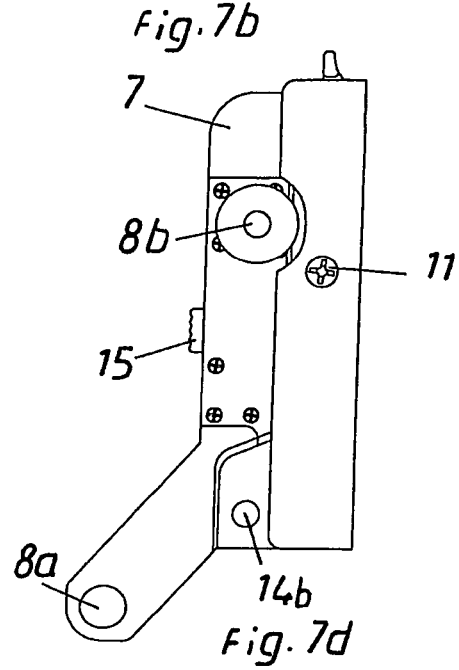
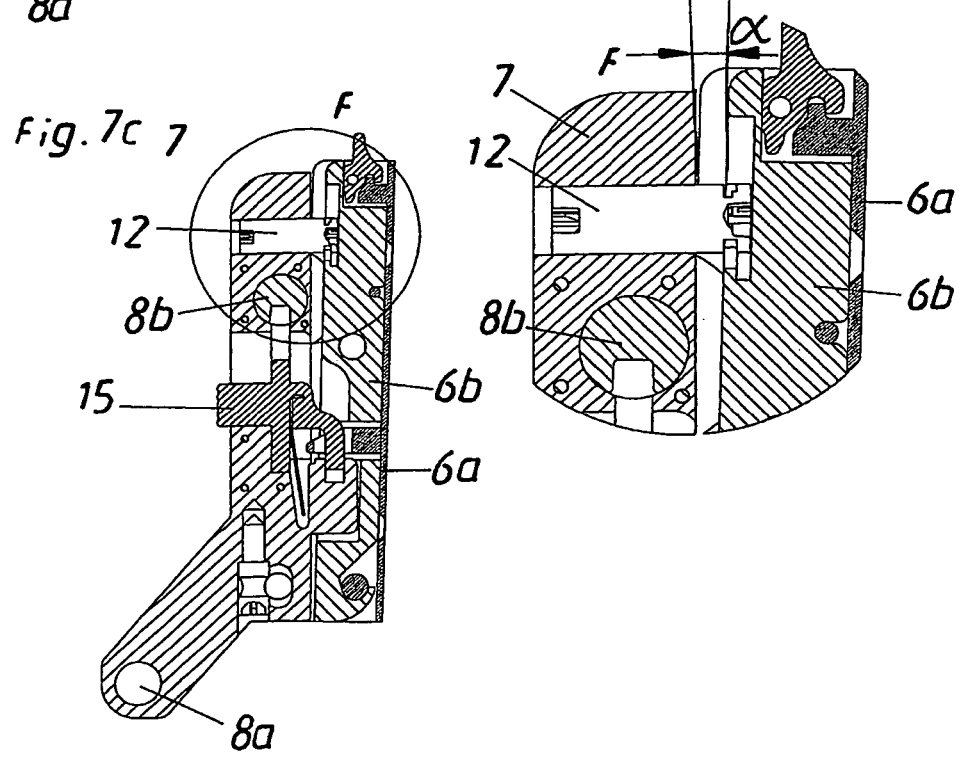

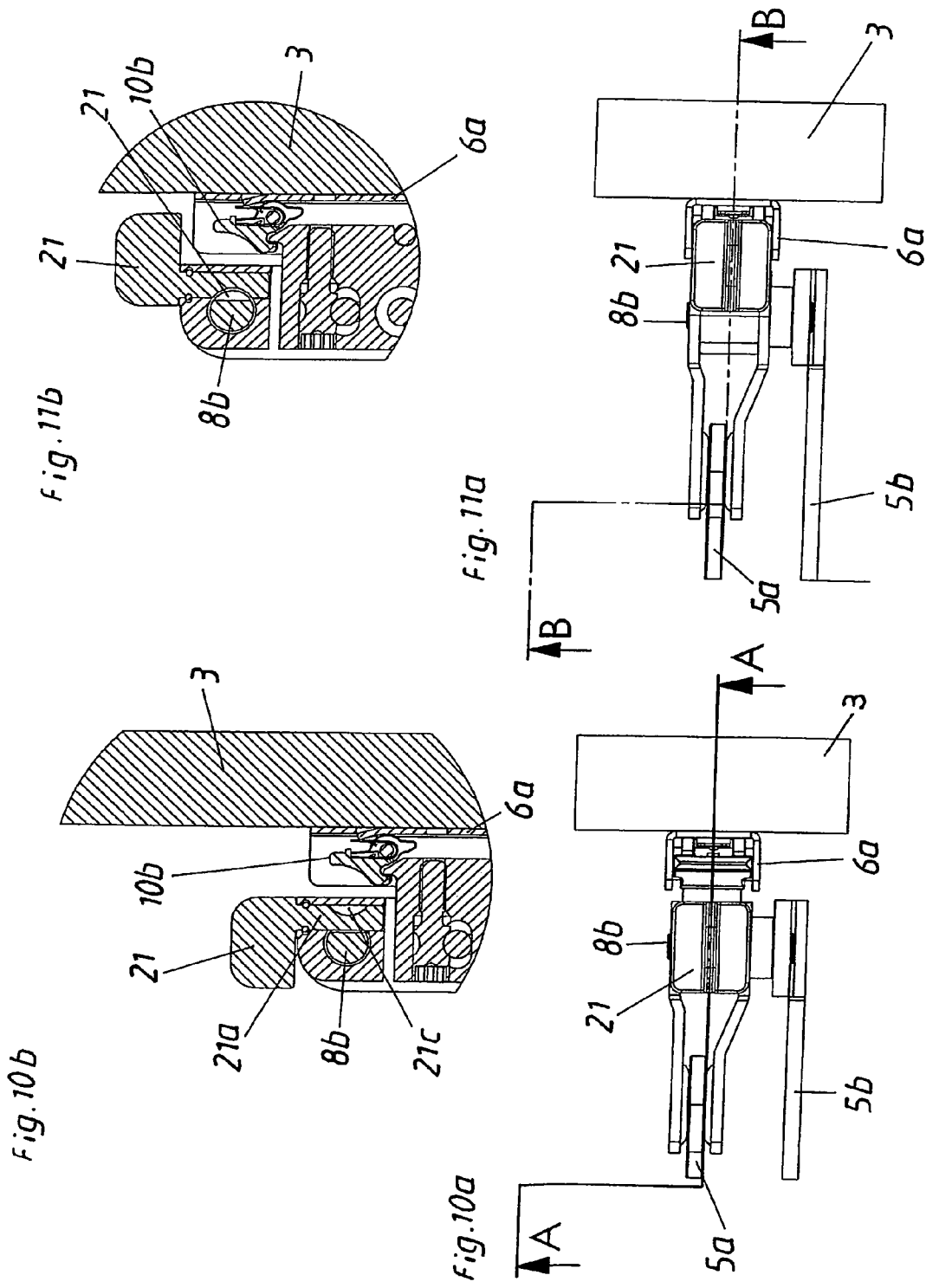

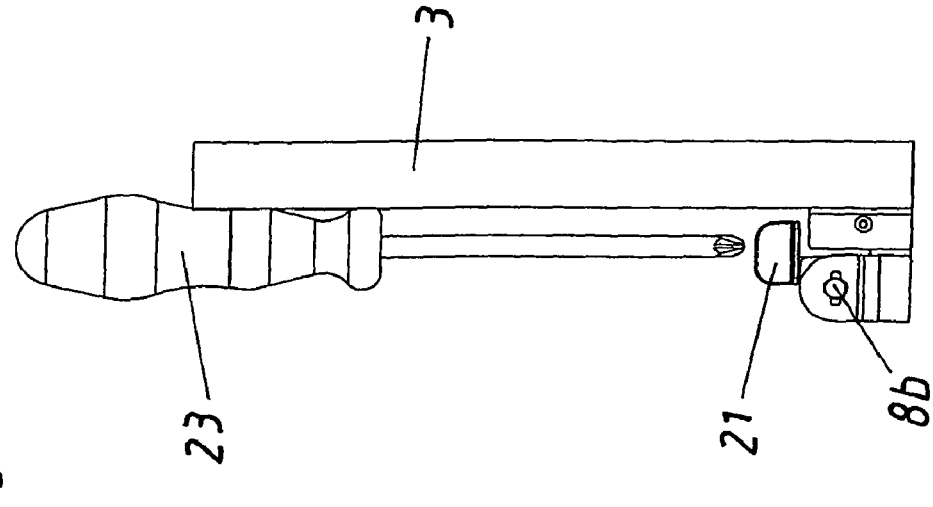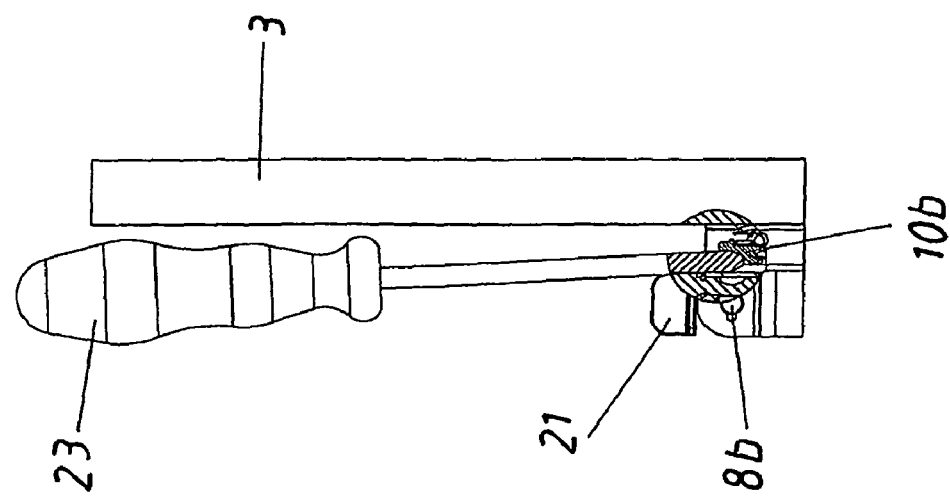

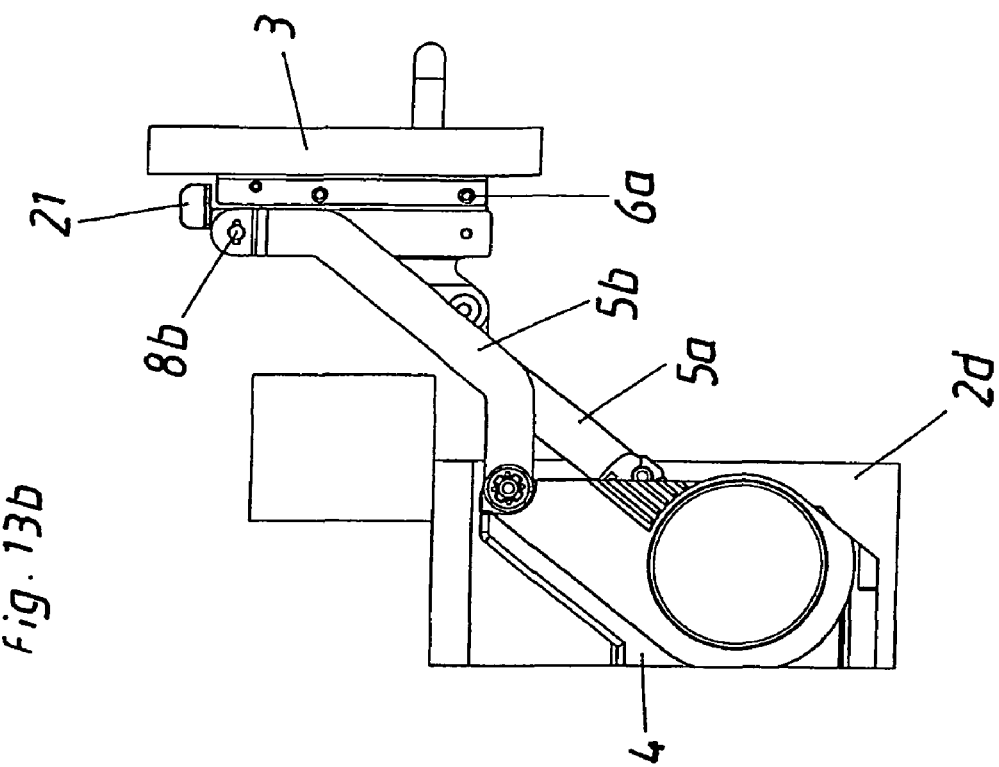
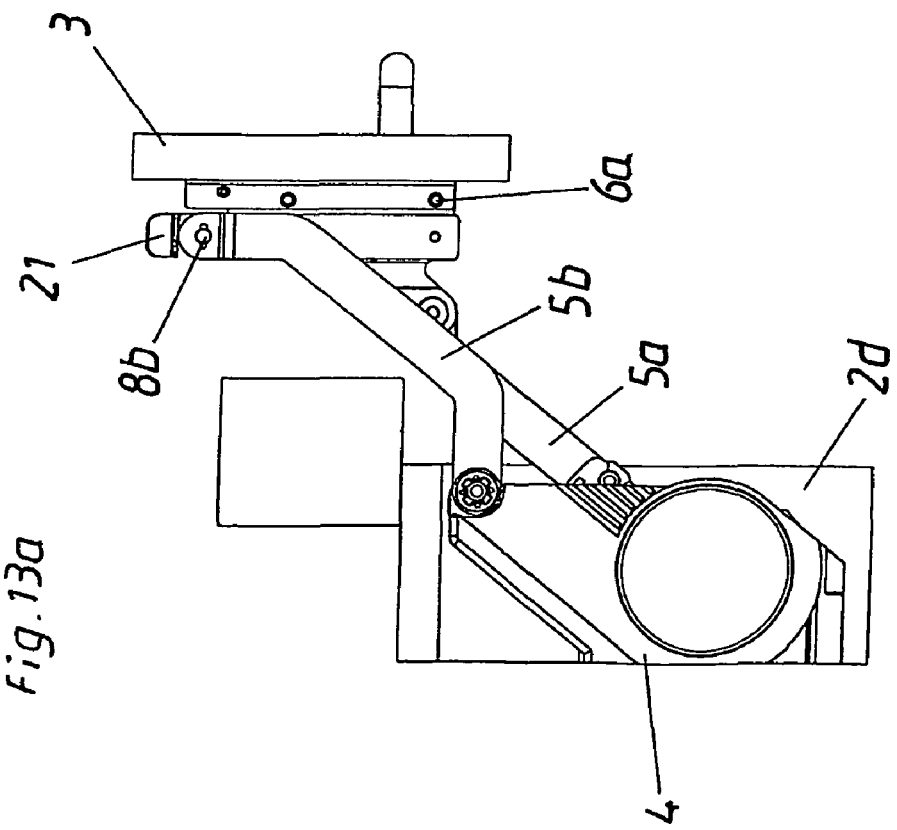

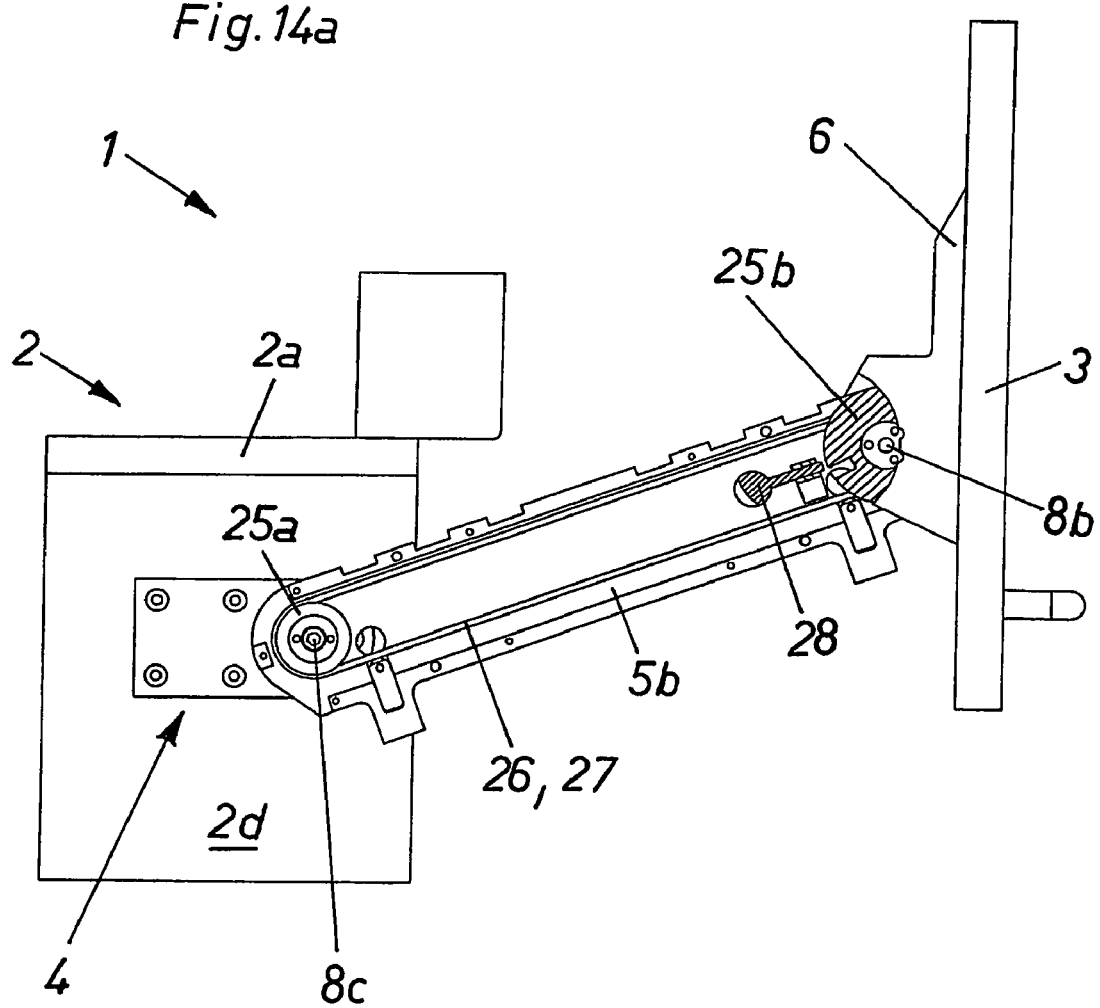

SHUTTER (OR DOOR) FITTING

This application is a continuation of International Application No. PCT/AT2006/000415, filed Oct. 10, 2006.

FIELD OF THE INVENTION

The present invention relates to a fitting for a flap for a swivellable attachment of a furniture flap to a cabinet body, with at least one actuating arm provided for moving the furniture flap, and with at least one flap-side fitting part which can be connected to the actuating arm.

DESCRIPTION OF THE RELATED ART

Such fittings for flaps are used, for example, in upper cabinets, such that the furniture flap can be opened upwards in relation to the furniture body. The actuating arm is attached with one end region to the furniture body or to a body-side fitting part, while the other end region of the actuating arm is attached to the flap-side fitting part. The furniture flap is attached to the furniture body by means of hinges on one side and connected on the other to the actuating arm which is provided to move the furniture flap from a closed position into an opening position. The fitting of the furniture flap in relation to the actuating arm is made difficult by the swivelling actuating arm, as this is unstable and can slide off into the furniture body when the flap is being attached.

It is therefore an object of the present invention to propose a fitting for a flap of the genre mentioned at the outset which allows a convenient fitting of the furniture flap.

SUMMARY OF THE INVENTION

The above objective is achieved according to the invention in an advantageous embodiment in which the flap-side fitting part comprises an anti-twist device for the temporary fixing of the swivel position of at least one actuating arm, preferably in a completely open position, wherein in a first operating position the anti-twist device locks the at least one actuating arm in its swivel position relative to the flap-side fitting part and in a second operating position allows a swivel movement of the actuating arm.

A first feature of the invention addresses the issue of facilitating the fitting of the furniture flap relative to the flap-side fitting part. To this end the relative position of the flap-side fitting part is locked in relation to the actuating arm by the proposed anti-twist device.

However, a further feature of the invention addresses the issue of, not only fixing the position of the flap-side fitting part relative to the actuating arm, but simultaneously locking the position of the actuating arm in relation to the cabinet body. The "empty" actuating arm, where the flap has not been yet attached, is preferably fixed in a completely open position in respect to its swivel position such that during fitting of the furniture flap this cannot slide off or spring up again due to a customary spring device (acting on the actuating arm, sometimes with very strong forces, to balance the weight of the flap) and in the process injure the installer.

According to a first variant of the invention it can be provided that on every side wall of the cabinet body at least two actuating arms, each having two pivot axes, are provided to move the furniture flap, wherein at least one pivot axis of said actuating arms can be locked by the anti-twist device. It may be expedient if the at least two actuating arms form a four-bar mechanism with the flap-side fitting part. If one pivot axis of such a four-bar mechanism is being locked, the remaining pivot axes of the four-bar mechanism are also fixed in position, with the result that the entire lever mechanism for moving the furniture flap for the fitting process is immobile.

According to an alternative variant of the invention, it can also be provided that on every side wall of the cabinet body only one actuating arm with two pivot axes is provided to move the furniture flap, wherein at least one additional cord, preferably a toothed belt, is guided between a guiding part housed rotation-resistant against the cabinet body and a further guiding part rotatably housed at the free end of the actuating arm and can be connected rotation-resistant to the flap-side fitting part, wherein the further guiding part can be locked relative to the adjusting arm by the anti-twist device. In other words, if only one actuating arm is provided to move the flap, an additional cord or a toothed belt brings about a forced guidance between the guiding part attached rotation-resistant to the cabinet body and the guiding part rotatably housed to the free end of the actuating arm. It is advantageous for the fitting of the flap if the anti-twist device has, attached to the actuating arm, a slider which can be brought into engagement with the further guiding part of the flap-side fitting part.

Once the flap has been fitted, the anti-twist device is deactivated, with the result that the customary movement path of the flap is not impeded.

According to an embodiment of the invention, it can be provided that the actuating arm has a pivot axis with a recess into which a locking part can be introduced. The design can be such that the recess runs radially to the pivot axis of the actuating arm. Alternatively, it may also be expedient if the recess runs across the pivot axis of the actuating arm.

In an advantageous embodiment of the invention it can be provided that the locking part is formed from a slider. However, it is also within the scope of the invention that the locking part is formed from a rotatable part.

According to a preferred embodiment of the invention, it can be provided that the flap-side fitting part has a base pre-fitted on the flap and an attachment part connected to the actuating arm. The design can be such that the attachment part can be connected to the base by a releasable attachment device, preferably a mechanical latching connection. In this connection, it can be expedient if the mechanical latching connection is formed such that the attachment part can be suspended into the base and then locked by being swivelled.

In this way, a convenient attachment of the flap in relation to the actuating arm is achieved; the actuating arm is fixed in a open position and the furniture flap with its pre-fitted base can be easily clipped onto the attachment part of the actuating arm.

According to the preferred embodiment of the invention, it can be provided that the attachment part is secured to the base, as well as to the releasable attachment device by a separate anti-lifting device. When using a mechanical latching connection, in particular with a spring-loaded clip lever, the possibility exists that the clip lever is unintentionally actuated, which would cause the flap to come loose or fall from the flap fitting. By providing an additional anti-lifting device the flap is doubly secured against falling and is thus held permanently to the flap fitting.

According to the preferred embodiment, it can be provided that the anti-lifting device comprises a spring-loaded slider which, in an operating position, can be brought into engagement with a safety catch attached to or formed on the base, or on the attachment part. In this connection, a structurally simple design can be achieved such that the anti-twist device is formed from the same slider as the anti-lifting device.

A further embodiment provides that the position of the actuating arm in relation to the flap-side fitting part can be adjusted by at least one setting device. Manufacturing tolerances and minor installation errors may lead to the formation of an unattractive seam, as the furniture flap is not optimally aligned in relation to the furniture body or to the furniture flaps of adjacent cabinets. In this way, unlike an embodiment known according to the state of the art, in which the actuating arm is merely hinged to the flap, an active influencing of the relative position between actuating arm (or a bearing part of same) and the flap-side fitting part is made possible. The setting device makes it possible for the installer to perform an individual and easy adjustment of the flap fitting in thereby achieving a visually attractive gap alignment.

According to the preferred embodiment it can be provided that the height of the actuating arm or its bearing part and/or its inclination and/or the lateral alignment in relation to the flap-side fitting part can be adjusted by the at least one setting device. Thus, an independent three-dimensional adjustment option for the actuating arm or its bearing part in relation to the flap-side fitting part or to the flap is made possible which permits an optimal adjustment of the already assembled flap. In this connection, the design can be such that in each case a separate setting device is provided to adjust the height, the inclination and the lateral alignment.

A three-dimensional setting of the bearing-point position of the at least one actuating arm relative to the flap-side base (preferably firmly screwed fast to the flap) is possible through the separate setting devices. The setting of the height H brings about a change in the previously-named bearing-point position in longitudinal extension of the furniture flap, while the setting of the lateral alignment B brings about a change in the bearing-point position along the width of the furniture flap. The height H and the lateral alignment B are thus preferably adjusted in two-dimensional XY-direction parallel to the flap plane, while the additional adjustment of the inclination a brings about an inclination adjustment of the actuating arm or its bearing part relative to the flap-side fitting part, which results in a change in the inclination of the flap plane relative to the end-surface plane of the cabinet body.

In a further advantageous embodiment, it can be provided that two actuating arms are directly or indirectly rotatably housed on the attachment part. An actuating arm and a control arm can preferably be used here, wherein the actuating arm is usually loaded body-side by a spring device to compensate for the weight of the flap. The control arm, on the other hand, determines the course of movement, i.e., the position of the flap in relation to the furniture body during its opening and closing movement.

A structurally simple design of the invention provides that the at least one setting device has at least one threaded screw which can be actuated manually or by a setting element, preferably a screwdriver. In this connection, it is, of course, also possible to provide, instead of the threaded screw, eccentrics or discs which are attached eccentrically on a shaft. Also, the design can be such that the setting device(s) has (have) at least one, preferably automatic, worm gear.

Further details and advantages of the present invention are described below in further detail using the description of the Figures, with reference to the drawings. There are shown in:

BRIEF DESCRIPTION OF THE DRAWINGS

FIGS. 1a, 1b a side view of a cupboard-shaped piece of furniture with an upwards-opening flap and a detailed representation of the flap fitting, FIGS. 2a-2c the flap-side flap fitting in an exploded representation, assembled and in a perspective view from the rear, FIGS. 3a, 3b a perspective representation of the flap fitting with twist-resistant pivot axis and a vertical section of the same, FIGS. 4a, 4b a perspective representation of the flap fitting with active anti-lifting device and a vertical section of the same, FIGS. 5a-5c different views of the completely locked flap fitting, FIGS. 6a-6d the flap fitting in different views when carrying out a height adjustment, FIGS. 7a-7d the flap fitting in different views when carrying out an inclination adjustment, FIGS. 8a-8c the flap fitting in different views when carrying out a lateral adjustment, FIGS. 9a, 9b an alternative embodiment of the anti-twist device with a rotatable part for locking the pivot axis of the actuating arm, FIGS. 10a, 10b the anti-twist device from FIGS. 9a, 9b, wherein the pivot axis of the actuating arm is locked, FIGS. 11a, 11b the anti-twist device from FIGS. 9a, 9b, wherein the pivot axis of the actuating arm can be moved freely, FIGS. 12a, 12b the flap-side fitting with the rotatable part of the anti-twist device, which allows the access of a screwdriver in one position and prevents the access of the screwdriver in a second position, FIGS. 13a, 13b side views of an actuating mechanism mounted on the furniture body with an actuating arm, secured against swivelling or swivellable, and FIGS. 14a, 14b a further variant of the invention with only one actuating arm to move the flap, with the anti-twist device in the passive and active position respectively.

DETAILED DESCRIPTION OF THE PREFERRED EMBODIMENT

Figure 8A:
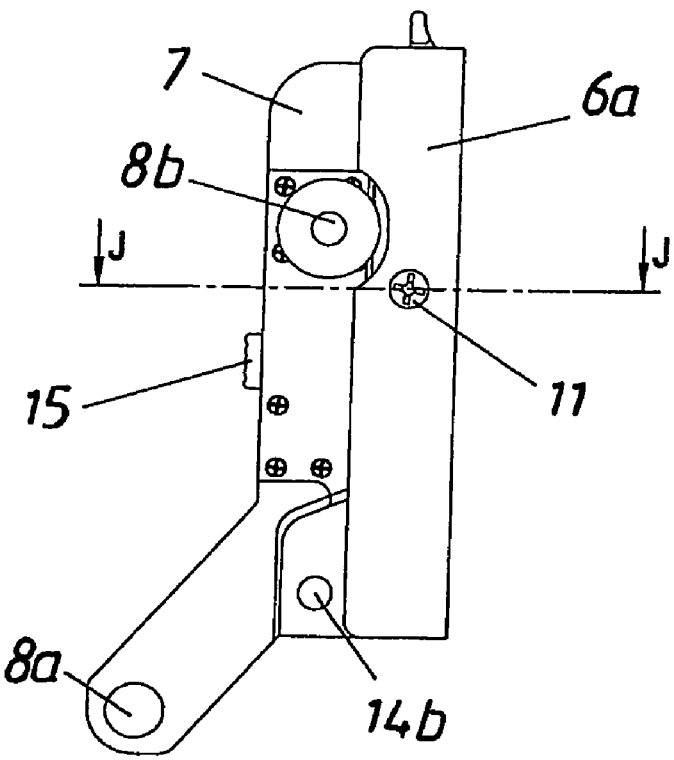

FIG. 1a shows a side view of a cupboard-shaped piece of furniture 1 with an upwards-opening flap 3. FIG. 1b shows the detail A from FIG. 1a. The cupboard-shaped piece of furniture 1 comprises in conventional manner a cabinet body 2, a cabinet top 2a, a rear wall 2b, a cabinet bottom 2c and two side walls 2d, on each of which an actuating mechanism 4 to move the flap 3 is mounted. The actuating mechanism 4 comprises a spring or drive device, to which no further reference will be made. The actuating mechanism 4 has two actuating arms 5a and 5b, which are provided to move the flap 3 between a closed position and an open position. The actuating arms 5a, 5b have pivot axes 8a, 8b, wherein at least one pivot axis 8a, 8b can be locked by an anti-twist device to be described in more detail. The actuating arms 5a, 5b form a four-bar mechanism with the pivot axes 8a, 8b.

FIG. 1b shows the detail A from FIG. 1a. On the back of the flap 3 a flap-side fitting part 6 is provided which is connected directly or indirectly via a releasable attachment device 10b to the bearing part 7 of the two actuating arms 5a and 5b. The two actuating arms 5a and 5b are housed on the bearing part 7 via pivot axes 8a, 8b, wherein the anti-twist device according to the invention, which is to be described in more detail, acts preferably on the pivot axis 8b.

FIG. 2a shows an exploded representation of an exemplary flap fitting. The flap-side fitting part 6 is formed in two parts and comprises a base 6a pre-fitted on the flap 3 and an attachment part 6b, connected to the actuating arms 5a and 5b, which can be locked to each other preferably via a spring-loaded mechanical latching connection 10a, 10b. The base 6a is pre-fitted on the inside of the flap 3, during fitting the attachment part 6b is firstly suspended with its recess 9b in the pins 9a and locked in the catch recess 10a by swivelling up with the help of the locking lever 10b. The attachment part 6b is formed somewhat narrower than the U-shaped base 6a, with the result that the attachment part 6b can be moved within the arms of the U-shaped base 6a with the help of the side adjustment screw 11. The pin 14b is housed stationary on the attachment part 6b, wherein an actuation of the height adjustment screw 13 changes the height of the bearing part 7 in relation to the attachment part 6b. The bearing pin 8c, which is provided for housing the actuating arm 5b shown in FIG. 2c, is located on the pivot axis 8b. The inclination adjustment screw 12 passes through the bearing part 7 and rests, when mounted, against the fitting part 6b, in order to bring about an inclination of the bearing part 7 in relation to the attachment part 6b. The slider 15, the function of which is described in more detail in the following Figures, comprises the locking part 15a (which is part of the anti-twist device for the actuating arm 5b) and the anti-lifting device 15b, which can be brought into engagement with the safety catch 16 of the base 6a. The slider 15 is spring-loaded by the leaf spring 15c, whereby the slider 15 is prevented from sliding off unintentionally.

FIG. 2b shows the flap fitting assembled. The parts 6a, 6b and 7 are connected to each other and form a unit which is connected on one side to the flap 3 (not shown) and on the other side to the actuating arms 5a and 5b (FIG. 2c). The unit, comprising the bearing part 7 and the attachment part 6b, can be released by the base 6a via the stop lever 10b. The bearing part 7 can be adjusted in height direction H relative to the attachment part 6b (and thus to the base) by the height adjustment screw 13, shown in FIG. 2a, which is accessible on the underside of the bearing part 7. The attachment part 6b can be adjusted its in lateral alignment B within the base 6a, U-shaped in cross-section, by the side adjustment screw 11. Finally, the bearing part 7 can be inclined by the angle α from the 0° position shown in FIG. 2b relative to the unit, comprising the base 6a and the attachment part 6b, by the inclination adjustment screw 12.

FIG. 2c shows the flap fitting with mounted actuating arms 5a and 5b from a rear perspective representation.

FIG. 3a shows a perspective front view of the flap fitting with mounted actuating arms 5a and 5b which are rotatably housed on the bearing part 7 via the pivot axes 8a and 8b. The flap-side fitting part 6 comprises the pre-fitted base 6a and the attachment part 6b which can be releasably connected to each other via a mechanical latching connection 10a, 10b. FIG. 3a and FIG. 3b show the start of the fitting process, wherein as a first step the attachment part 6b is suspended into the pin 9a of the base 6a. Reference is made below to the vertical section of the flap fitting according to FIG. 3b in which the operation of the anti-twist device is explained in more detail. The actuating arms 5a, 5b each have two pivot axes 8a, 8b, with the result that these form a four-bar mechanism with the flap-side fitting part 6 through their body-side articulation. The actuating arm 5b bears against the pivot axis 8b, which according to FIG. 3b engages with the locking part 15a attached to the slider 15, whereby the pivot axis 8b of the actuating arm 5b is locked in its swivel position relative to the flap-side fitting part 6a, 6b. Because its pivot axis 8b is locked, the actuating arm 5b cannot be swivelled in relation to the furniture body 2 nor in relation to the flap-side fitting part 6a, 6b, whereby a simple and rapid fitting of the flap 3 is made possible. The leaf spring 15c rests against the attachment part 6b and prevents an unintended releasing of the slider 15. The anti-lifting device 15b, which can be brought into engagement with the safety catch 16 attached to the base 6a, but which is inactive in the Figure shown, can also be seen. The inclination adjustment screw 12 rests with its end against the attachment part 6b and upon twisting of the same brings about an inclination adjustment of the bearing part 7 in relation to the attachment part 6b. The bearing part 7 can be adjusted according to the length of the oblong hole 14a by the height adjustment screw 13, in the concave or tapered section of which the pin 14b is housed, whereby the height of the bearing part 7 can be adjusted in relation to the attachment part 6b.

FIG. 4a further shows the perspective front view of the flap fitting from FIG. 3a, with the difference that the unit comprising the bearing part 7 and the attachment part 6b, has been swivelled closer to the base 6a and the slider 15 has been pushed into its second operating position. The vertical section according to FIG. 4b shows that the locking part 15a has been disengaged from the pivot axis 9a by the displacement of the slider 15, with the result that all pivot axes 8a, 8b and, thus the actuating arms 5a, 5b, can now move freely. The recess 20, which runs radially to the pivot axis 8b and into which the locking part 15a of the slider 15 can be introduced, can also be seen (the recess 20 being located in the bearing pin 8c which is located on the pivot axis 8b as previously described herein and shown in FIGS. 2a, 2b, 3a, and 3b). The slider 15 also fulfils a double function, as the anti-lifting device 15b now also engages with the safety catch 16. If the latching connection 10a, 10b is unintentionally released, the unit, comprising the bearing part 7 and the attachment part 6b, can be only partially released from the pre-fitted base 6a and is therefore secured permanently against a fall of the flap 3.

FIG. 5a shows the completely locked position of the bearing part 7/attachment part 6b unit with the base 6a pre-fitted on the flap 3. FIG. 5b shows a top view of the flap fitting with its actuating arms 5a and 5b, while FIG. 5c shows the vertical section along the line C-C from FIG. 5b. According to FIG. 5c the locking lever 10b is locked in, the pivot axis 8b is released from the locking part 15a and the anti-lifting device 15b of the slider 15 engages with the safety catch 16, with the result that the flap 3 is doubly secured against falling, on one side by the latching connection 10a, 10b and on the other side by the anti-lifting device 15b. This shown position of the slider 15 corresponds to the in-use position during normal operation of the flap fitting.

FIGS. 6a to 6d show different views of the flap fitting, in which the height adjustment procedure is explained. FIG. 6a shows a side view of the base 6a which is pre-fitted on a flap 3, not represented. The bearing part 7/attachment part 6b unit has been clipped onto the base 6a via a mechanical latching connection (locking lever 10b). The bearing part 7 can be adjusted by the differential height ΔH relative to the attachment part 6b by the height adjustment screw 13 shown in FIG. 6c. FIG. 6b shows the flap fitting from FIG. 6a, with the height H of the bearing part 7 adjusted. FIG. 6c shows a vertical section through the flap fitting, in which the height adjustment screw 13, provided to adjust the height of the flap 3, is represented. This height adjustment screw 13 rests with its tapered section on the pin 14b. The pin 14b is housed stationary on the attachment part 6b, wherein the height of the bearing part 7 is adjusted upon actuation of the height adjustment screw 13, and wherein the maximum height adjustment corresponds to the extent of the oblong hole 14a. FIG. 6d shows the detailed view G of the circle from FIG. 6c.

FIGS. 7a to 7d show different views of the flap fitting, in which the inclination adjustment procedure is explained. FIG. 7a shows a side view of the flap fitting with slightly inclined bearing part 7 in relation to the base 6a/attachment part 6b unit, while FIG. 7b shows the parallel alignment (0° inclination) of the bearing part 7. FIG. 7c shows a vertical view through the flap fitting, wherein the inclination α can be changed by screwing in the inclination adjustment screw 12, which on one side cooperates with an internal thread of the bearing part 7 and on the other side rests at its rear end on the attachment part 6b. By screwing the inclination adjustment screw 12 clockwise the inclination angle α is increased, and decreased correspondingly when screwed counter clockwise. FIG. 7d shows the detail F from FIG. 7c with the bearing part 7 adjusted by the inclination angle α.

Figure 8B:
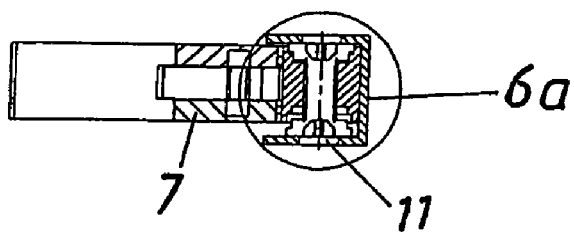
Figure 8C:
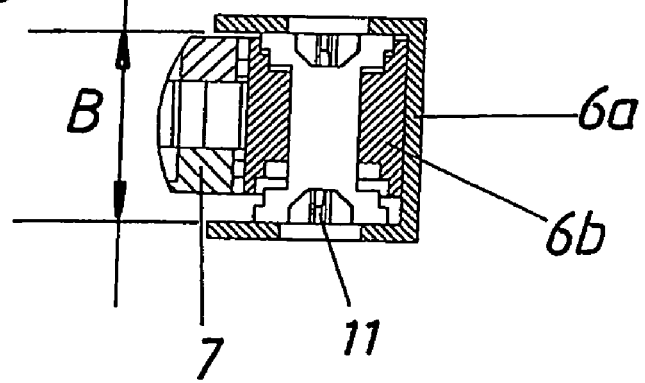

FIGS. 8a to 8c show different views of the flap fitting in which the lateral alignment or transverse adjustment procedure of the bearing part 7/attachment part 6b unit relative to the base 6a is explained. FIG. 8a shows a side view of the flap fitting with the side adjustment screw 11. FIG. 8b shows a section in the direction of the arrow J-J from FIG. 8a, while FIG. 8c shows the enlarged detail from FIG. 8b. The side adjustment screw 11 is situated between the two arms of the U-shaped base 6a and is housed there stationary but rotatable. The side adjustment screw 11 has an external thread which engages with an internal thread of the attachment part 6b. When the side adjustment screw 11 is screwed the width B of the attachment part 6b with its bearing part 7 attached thereto can thus be adjusted, wherein the maximum width adjustment corresponds to the distance between the two arms of the U-shaped base 6a.

Figure 9B:
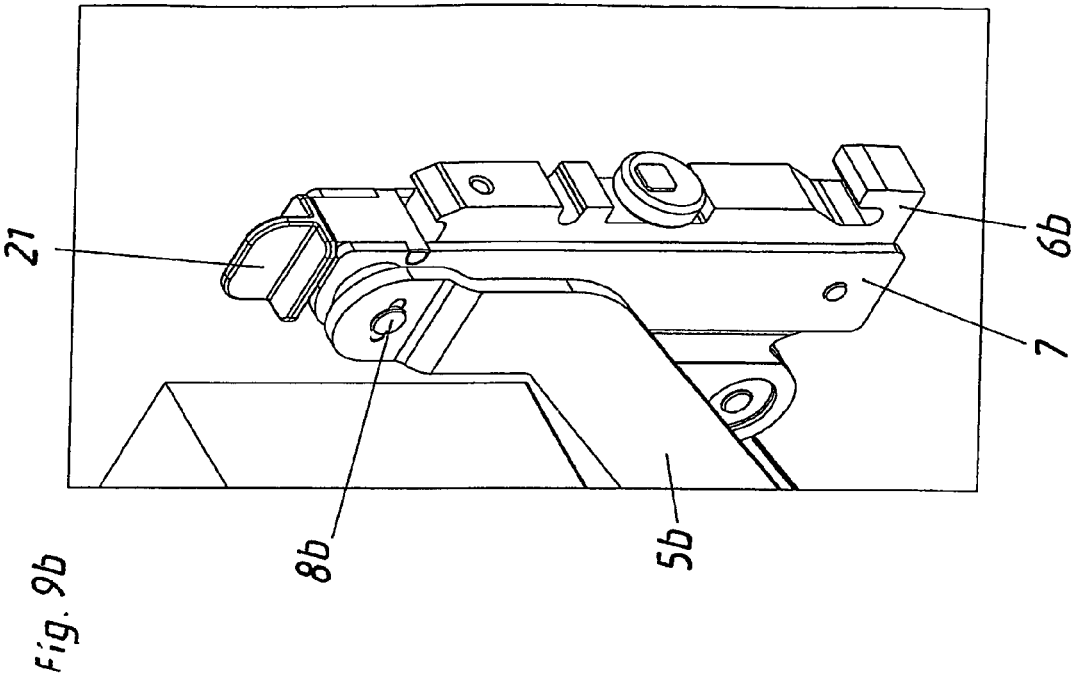
Figure 9A:
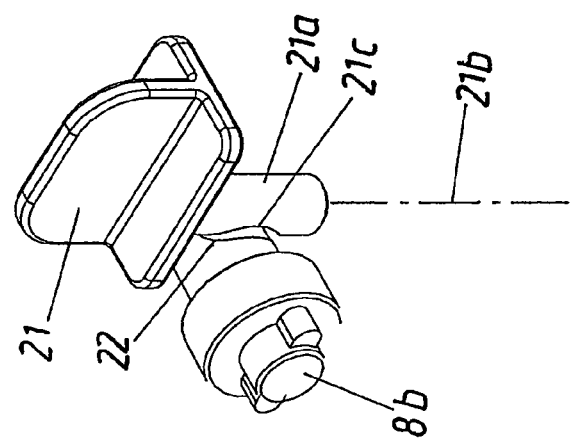

FIG. 9a and FIG. 9b show an alternative embodiment example of the anti-twist device of the actuating arm 5b. Instead of the slider 15 shown in FIGS. 1 to 8 a rotatable part 21 is provided which in a first rotation position locks the pivot axis 8b in its swivel position and in a further rotation position permits a swivel movement of the pivot axis 8b and thereby also a swivelling of the actuating arm 5b. The rotatable part 21 comprises a locking part in the form of a cylinder 21a with a cylinder axis 21b. The cylinder 21a has a cylindrical recess 21c which runs across the cylinder axis 21b. The cylindrical part of the pivot axis 8b also has a cylindrical depression 22 which runs across the longitudinal extension of the pivot axis 8b. A twisting movement of the pivot axis 8b is possible in the rotation position shown in FIG. 9a of the rotatable part 21.

FIG. 9b shows this alternative anti-twist device on the flap-side furniture fitting with the bearing part 7/attachment part 6b unit. The actuating arm 5b bears swivellable against the pivot axis 8b and in the shown rotation position of the rotatable part 21, is not locked in its swivel position.

FIG. 10a shows a top view of the flap fitting mounted on the flap 3 with the anti-twist device shown in FIGS. 9a and 9b. The base 6a is mounted on the flap 3 and releasably connected to the bearing part 7/attachment part 6b unit against which the two actuating arms 5a and 5b bear. FIG. 10b shows the sectional representation in the direction of the arrow A-A from FIG. 10a. The rotatable part 21 is located in the rotation position in which it fixes the pivot axis 8b in its swivel position, as the recess 21c of the rotatable part 21 is facing away from the pivot axis 8b. A twisting of the pivot axis 8b of the actuating arm 5b is not possible in the position shown in FIG. 10a and FIG. 10b of the rotatable part 21.

FIGS. 11a and 11b show analogously the rotation position of the rotatable part 21 in which a twisting movement of the pivot axis 8b of the actuating arm 5b is possible. By rotating the rotatable part 21 by 180°, the cylindrical depression 21 has been screwed towards the pivot axis 8b, with the result that the corresponding depressions 21c and 22 (FIG. 9a) permit a rotary movement of the actuating arm 5b. A particular advantage in the embodiment with this rotatable part 21 is, because of the rotation position shown in FIG. 11a of the rotatable part 21, access to the locking lever 10b is not possible. In addition to impeding the swivel movement, the rotatable part 21 fulfils a further function, namely that the locking lever 10b is unintentionally reached by the screwdriver. Unlike the active anti-lifting device 15b shown in FIG. 4b which can be brought into engagement with the safety catch 16, a passive safeguard against lifting is achieved by the rotation position of the rotatable part 21.

FIG. 12a and FIG. 12b show this passive safeguard according to the rotation position of the rotatable part 21. In the position shown in FIG. 12a of the rotatable part 21 the locking lever 10b can be actuated with a screwdriver 23, while in the rotation position shown in FIG. 12b of the rotatable part 21 an introduction of the screwdriver 23 is not possible.

FIG. 13a and FIG. 13b show the embodiment of the rotatable part 21 according to FIGS. 9 to 12, which is part of the anti-twist device for the actuating arm 5b. An actuating mechanism 4 with two actuating arms 5a and 5b is mounted on the side wall 2d of a cupboard-shaped piece of furniture. FIG. 13a shows the completely open position of the flap 3, wherein the pivot axis 8b is locked in its swivel position by the rotation position of the rotatable part 21 and an introduction of a screwdriver from above into the locking lever 10b, not shown, in the base 6a is also possible. FIG. 13b shows on the other hand the position twisted by 180° of the rotatable part 21, wherein in this position the pivot axis 8b of the actuating arm 5b is not locked. According to this Figure a swivelling of the actuating arms 5a and 5b is possible, but access to the locking lever 10b of the releasable attachment device is denied.

FIG. 14a schematically shows a variant of the invention. The piece of furniture 1 comprises a cabinet body 2 with a cabinet top 2a and a side wall 2d. Arranged on every side wall 2d of the cabinet body 2 is an actuating mechanism 4 which has only one actuating arm 5b with two pivot axes 8b and 8c to move the furniture flap 3. A guiding part 25a housed rotation-resistant (e.g. a rotation-resistant toothed wheel) is arranged coaxial to the pivot axis 8c, wherein a cord 26, preferably a toothed belt 27, is guided over a further guiding part 25b (preferably a further toothed wheel). On the other hand, the further guiding part 25b is rotatably housed on the free end of the actuating arm 5b and is, however, connected rotation-resistant to the flap-side fitting part 6. A forced guidance between the rotation-resistant guiding part 25a and the rotatable guiding part 25b (and thus of the flap-side fitting part 6 or the furniture flap 3) is made possible via the toothed belt 27, with the result that the furniture flap 3 is guided constantly parallel to the front face of the furniture body 2 during its movement. A schematically represented slider 28, which can be brought into engagement in a corresponding recess of the guiding part 25b, can be seen at the free end of the actuating arm 5b. The slider 28 is part of the anti-twist device, which is deactivated however in the shown Figure, i.e. the furniture flap 3 is substantially freely movable between a closing and an opening position.

Figure 14B:
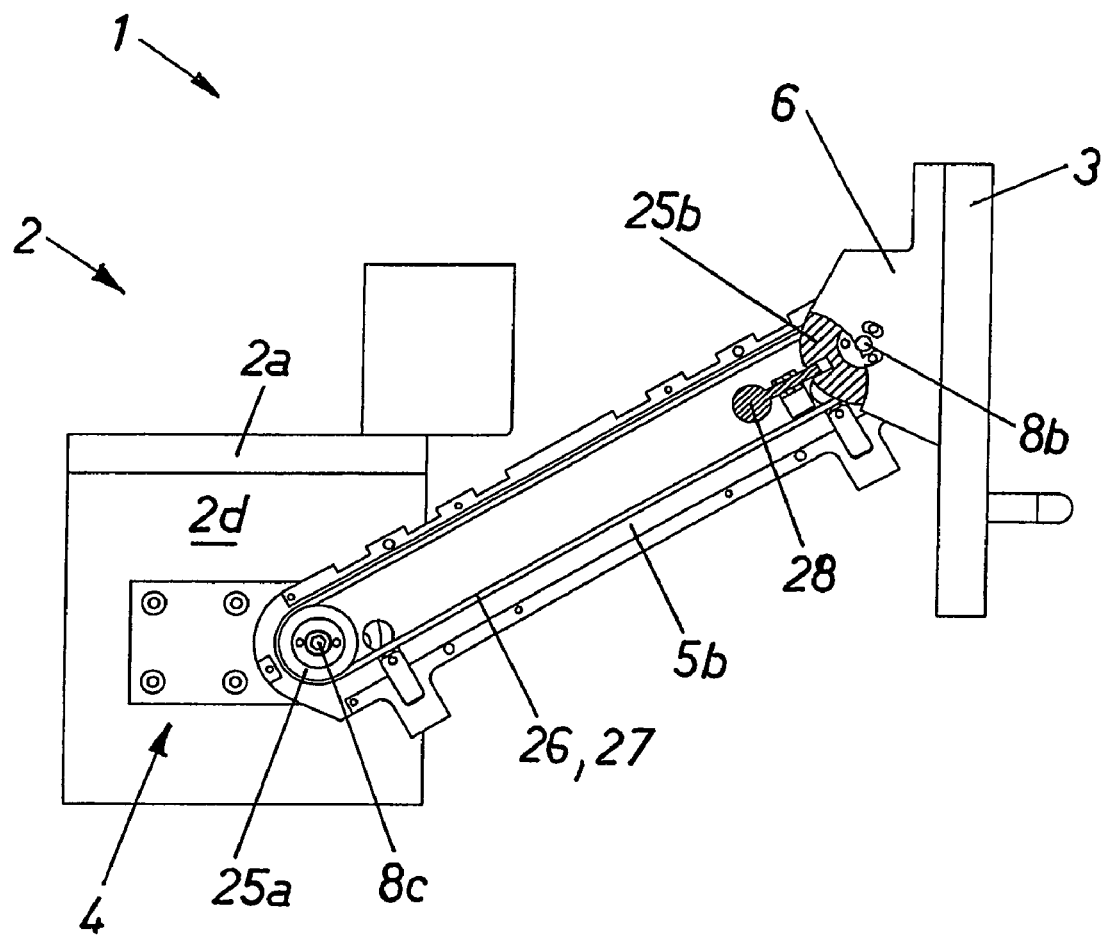

FIG. 14b shows, on the other hand, the position of the slider 28 in which this engages in the recess of the guiding part 25b. Thus, in addition to the rotation-resistant guiding part 25a on the cabinet body, the further guiding part 25b is also temporarily not rotatable and the toothed belt 27 keeps the actuating arm 5b in its completely open position, with the result that the furniture flap 3 can be conveniently fitted on the flap-side fitting part 6, lockable relative to the actuating arm 5b, without the added risk that the actuating arm 5 can slide off into the furniture body or spring up again by an impinging spring device and in the process cause injuries.

The present invention is not limited to the shown embodiment examples, but covers or extends to all variants and technical equivalents which may fall within the scope of the following claims. Also, the chosen positions in the description such as e.g. above, below, laterally etc. are related to the customary installation position of the shutter fitting or to the directly described and represented Figure and are to be transferred accordingly to the new position in the event of a change in position. The anti-twist device according to the invention can also be realized by providing a clamping device 8b gripping round the pivot axis 8b. It also lies within the scope of the invention to arrange clamping eccentrics or similar for this purpose.

The invention claimed is:

1. A flap fitting for a swivellable attachment of a furniture flap to a cabinet body, said flap fitting comprising:
    at least one actuating arm provided for moving the furniture flap;
    an anti-lifting device having a spring loaded slider;
    a releasable attachment device; and
    at least one flap side fitting part which can be connected to said at least one actuating arm, said flap side fitting part having an anti-twist device for temporary fixing of a swivel position of said at least one actuating arm, a base pre-fitted on the furniture flap, and an attachment part connected to said at least one actuating arm, and said anti-twist device having a spring loaded slider,
    wherein said attachment part is connected to said base by said releasable attachment device or a mechanical latching connection, and said attachment part and said releasable attachment device form an interconnected unit that is secured to the base by said anti-lifting device,
    wherein when in a first operating position, said anti-twist device is configured to lock said at least one actuating arm in the swivel position relative to said flap side fitting part,
    wherein when in a second operating position, said anti-twist device is configured to allow a swivel movement of said at least one actuating arm,
    wherein the spring loaded slider of said anti-lifting device is configured to be brought into engagement with a safety catch attached to, or formed on, said base or on said attachment part, and
    wherein the spring loaded slider of said anti-twist device is the same spring loaded slider of said anti-lifting device.

2. The flap fitting according to claim 1, wherein said anti-twist device locks said at least one actuating arm in the open position.

3. The flap fitting according to claim 1,
    wherein said at least one actuating arm is at least two actuating arms,
    wherein said at least two actuating arms are provided on one or more side walls of the cabinet body to move the furniture flap,
    wherein each of said at least two actuating arms has two pivot axes, and
    wherein at least one of said pivot axes of said at least two actuating arms can be locked by said anti-twist device.

4. The flap fitting according to claim 1,
    wherein said at least one actuating arm has a pivot axle with a recess into which a locking part is introducible, and
    wherein the recess runs radially to the pivot axle of said at least one actuating arm.

5. The flap fitting according to claim 1, wherein said flap side fitting part has a base pre-fitted on the furniture flap and an attachment part connected to said at least one actuating arm.

6. The flap fitting according to claim 5, further comprising a mechanical latching connection,
    wherein said attachment part can be connected to said base by said mechanical latching connection.

7. The flap fitting according to claim 6, wherein said mechanical latching connection is formed such that said attachment part can be supported by said base and then locked to said base by swiveling.

8. The flap fitting according to claim 5, further comprising a releasable attachment device,
    wherein said attachment part can be connected to said base by said releasable attachment device.

9. The flap fitting according to claim 1, further comprising at least one screw,
    wherein a position of said at least one actuating arm in relation to said flap side fitting part can be adjusted by said at least one screw.

10. The flap fitting according to claim 9, wherein at least one of the group consisting of height adjustment of said at least one actuating arm, inclination of said at least one actuating arm and lateral alignment of said at least one actuating arm in relation to said flap side fitting part can be adjusted by said at least one screw.

11. The flap fitting according to claim 10, further comprising a separate screw,
    wherein the height adjustment of said at least one actuating arm, the inclination of said at least one actuating arm and the lateral alignment of said at least one actuating arm in relation to said flap side fitting part can be adjusted by said separate screw.

12. The flap fitting according to claim 9, wherein said at least one screw can be actuated manually or by a screwdriver.

13. The flap fitting according to claim 1, wherein said at least one actuating arm is rotatably housed at said flap side fitting part.

* * * * *